United States Patent [19]

Hammerslag

[11] Patent Number: 5,460,170
[45] Date of Patent: Oct. 24, 1995

[54] ADJUSTABLE SURGICAL RETRACTOR

[76] Inventor: Julius G. Hammerslag, P.O. Box 4741, San Clemente, Calif. 92674

[21] Appl. No.: 294,330

[22] Filed: Aug. 23, 1994

[51] Int. Cl.$^6$ ................................................. A61M 29/02
[52] U.S. Cl. ........................... 600/201; 606/198; 604/104
[58] Field of Search .............................. 128/20; 606/190, 606/191, 198, 200; 604/104–109, 174, 178

[56] References Cited

U.S. PATENT DOCUMENTS

| | | |
|---|---|---|
| 2,812,758 | 11/1957 | Blumenschein . |
| 3,782,370 | 1/1974 | McDonald . |
| 3,807,393 | 4/1974 | McDonald . |
| 4,177,802 | 12/1979 | Ogami . |
| 4,334,652 | 6/1982 | Blackburn . |
| 4,459,978 | 7/1984 | Kotsanis . |
| 4,502,485 | 3/1985 | Burgin . |
| 4,585,000 | 4/1986 | Hershenson . |
| 4,654,028 | 3/1987 | Suma . |
| 4,716,901 | 1/1988 | Jackson et al. . |
| 4,984,564 | 1/1991 | Yuen . |
| 5,062,847 | 11/1991 | Barnes . |
| 5,178,133 | 1/1993 | Pena . |
| 5,183,464 | 2/1993 | Dubrul et al. . |
| 5,197,971 | 3/1993 | Bonutti ............................. 606/198 X |
| 5,203,773 | 4/1993 | Green . |
| 5,232,451 | 8/1993 | Freitas et al. ..................... 606/191 X |
| 5,267,554 | 12/1993 | Wilk . |
| 5,273,026 | 12/1993 | Wilk . |
| 5,273,529 | 12/1993 | Idowu . |

FOREIGN PATENT DOCUMENTS

| | | | |
|---|---|---|---|
| 480653A | 4/1992 | European Pat. Off. ............... | 604/174 |
| 0539125 | 10/1992 | European Pat. Off. . | |
| 1234923 | 2/1967 | Germany .............................. | 606/198 |
| 474620 | 12/1953 | Italy ....................................... | 604/105 |
| 8000034 | 8/1981 | Japan . | |
| 404336059 | 11/1992 | Netherlands . | |
| 1367948 | 4/1986 | U.S.S.R. . | |

OTHER PUBLICATIONS

*Balloon Dilatation and Insertion of a Self–Expandable Flexible Metallic Stant in a Benign Stricture of the Left Hepatic Duct: Case Report*, CardioVascular and Interventional Radiology, (1989).

*Advances in Endoluminal Laparoscopy*, Lawrence Way, M. D., InnerDyne™ Medical, Inc.

*Primary Examiner*—Richard J. Apley
*Assistant Examiner*—Beverly M. Flanagan
*Attorney, Agent, or Firm*—Knobbe, Martens, Olson & Bear

[57] ABSTRACT

Disclosed is a self-retaining surgical retractor suitable for use in small surgical incisions or punctures, able to expand the incision or puncture to one or more enlarged cross-sectional areas and designed to protect the edges of the incision or puncture. The surgical retractor comprises a radially expandable tubular body having a control at the proximal end. Pull wires couple the control to the tubular body such that force applied to the control is transmitted to the tubular body as axially compressive force.

26 Claims, 6 Drawing Sheets

ADJUSTABLE SURGICAL RETRACTOR

FIELD OF THE INVENTION

This invention relates to devices for retracting the edges of incisions made in biological tissue and more particularly to devices for enlarging the cross-sectional area of an incision made in the skin during surgical procedures.

BACKGROUND OF THE INVENTION

Surgical procedures commonly involve incising or puncturing the skin or other biological tissue. Once a surgical incision is made in the skin, the natural elasticity of this tissue will tend to close the wound. Therefore, it is necessary to retract the edges of the incision to visualize and access underlying structures.

A variety of retractors have been developed for these purposes. Many retractors involve flat plates or tissue gripping structures at the ends of two hinge-connected arms. The edges of the incision are moved apart by inserting the flat plates or tissue gripping structures into the incision and separating the plates or gripping structures by activating the hinge.

One problem with many existing retractors is that they do not provide full protection to the edges of the incision from trauma caused by advancing instrumentation through the incision. Trauma to the edges of the incision decreases the amount of contamination needed to cause a wound infection by compromising the natural ability of cleanly incised biological tissue to resist infection.

Further, many retractors do not protect the edges of an incision from exposure to cancer cells and infective agents during extraction of tissue through the incision. This failure increases the incidence of both cancer in the incision tract and wound infections.

In addition, there has been a trend in recent years towards replacing conventional open surgical procedures with laparoscopic and endoscopic procedures. These minimally invasive procedures require small incisions often having a diameter of less than about five centimeters. Biopsies of the breast and other tissues also frequently require small incisions.

Retraction of the edges of a small laparoscopic incision is often accomplished by placing a canula in the incision. Widening the incision involves replacing the canula with canulae having successively larger cross-sectional areas. This process is time consuming and adds to the expense of the procedure.

Hence, there is a need for a self-retaining retractor that can be used in small incisions, that can adjustably expand the edges of the incisions, and that can protect the edges of an incision from trauma caused by the introduction of instrumentation and during the extraction of tissue. The present invention is an incision retractor suitable for use in small surgical incisions, able to expand the incision to a plurality of cross-sectional areas and designed to overcome the problems inherent in the prior art by increasing the protection provided to the edges of the incision. Thus, the present invention is designed to increase the ease of performing surgical procedures, particularly those utilizing small incisions, and to increase the likelihood of uneventful healing following surgery.

SUMMARY OF THE INVENTION

In accordance with one aspect of the present invention, there is provided a surgical retractor capable of reversibly expanding an incision in biological tissue from a first cross-sectional area to a second larger cross-sectional area. In one embodiment, the surgical retractor comprises a radially expandable tubular body having an axial lumen therethrough and a tubular wall surrounding the axial lumen. The tubular wall has an interior surface adjacent the axial lumen and an exterior surface on the radial exterior of the tubular wall. Between the interior surface and the exterior surface is a wall thickness. The tubular body also has opposing axial ends one of which is a proximal end and the other of which is a distal end provided with an atraumatic tip. Between the proximal end and the distal end is an axial length. The tubular body further has a plurality of segments, wherein at least one segment is a proximal segment adjacent to the proximal end and at least an additional segment is a distal segment adjacent to the distal end. The surgical retractor further comprises a control for applying an axially compressive force to the tubular body thereby reversibly expanding at least one segment of the tubular body from a first cross-sectional area to at least one second larger cross-sectional area while simultaneously shortening the axial length of the tubular body from a first axial length to at least one second shorter axial length. The control is connected to the proximal segment.

In accordance with another aspect of the present invention, there is provided a method of expanding an incision or puncture in biological tissue from a first cross-sectional area to a second larger cross-sectional area, by providing a surgical retractor according to one embodiment of the present invention, placing the surgical retractor into an incision in biological tissue, and activating the control to cause expansion of the tubular body from a first cross-sectional area to a second larger cross-sectional area while simultaneously shortening the axial length of the tubular body. Expansion of the tubular body cross-sectional area causes a corresponding expansion in the incision.

In accordance with another aspect of the present invention, there is provided a method of treating a mammal by providing a surgical retractor according to one embodiment of the present invention, placing the surgical retractor into an incision in biological tissue, and activating the control to cause radial expansion of the tubular body from a first cross-sectional area to a second larger cross-sectional area while simultaneously shortening the axial length of the tubular body. Expansion of the tubular body cross-sectional area causes a corresponding expansion in the incision. Instrumentation is then inserted into and removed from the axial lumen to effectuate treatment. The control is then actuated causing contraction of the tubular body from the second larger cross-sectional area to the first smaller cross-sectional area while simultaneously lengthening the axial length of the tubular body, thereby permitting a corresponding contraction in the incision. Finally, the surgical retractor is removed from the incision.

In accordance with another aspect of the present invention, there is provided an adjustable puncture expander. The adjustable puncture expander comprises a radially expandable tubular body having a proximal end and a distal end and is expandable from a first cross-sectional area to a second, larger cross-sectional area upon axial compression thereof. The adjustable puncture expander further comprises a control on the proximal end of the tubular body, and at least two pull wires extending distally from the control to a point of attachment to the tubular body. Activation of the control advances the pull wires in an axial, proximal direction causing an axial compression of the tubular body and radial expansion of at least a segment of the tubular body from the first cross-sectional area to the second, larger cross-sectional area. The tubular body can comprise an expandable tubular mesh. At least one of the pull wires of the adjustable puncture expander can extend distally along the mesh from the control, through the mesh, and then proximally along the mesh back toward the control. Further, the adjustable puncture expander can comprise a tubular elastic sleeve surrounding the tubular mesh.

DETAILED DESCRIPTION OF THE PREFERRED EMBODIMENTS

In one embodiment, the present invention is an improved self-retaining surgical retractor suitable for use in small surgical incisions or punctures, able to expand the incision to a plurality of cross-sectional areas and designed to overcome the problems inherent in the prior art by increasing the protection provided to the edges of the incision or puncture. The surgical retractor comprises a radially expandable tubular body having a control at the proximal end. Pull wires couple the control to the tubular body such that force applied to the control is transmitted to the tubular body as axially compressive force.

As used herein, "incision" and "puncture" are interchangeably used to refer to an opening in biological tissue, whether naturally or non-naturally occurring. The relative proportions shown in the Figures are illustrative only, and are not necessarily drawn to scale.

Figure 1:
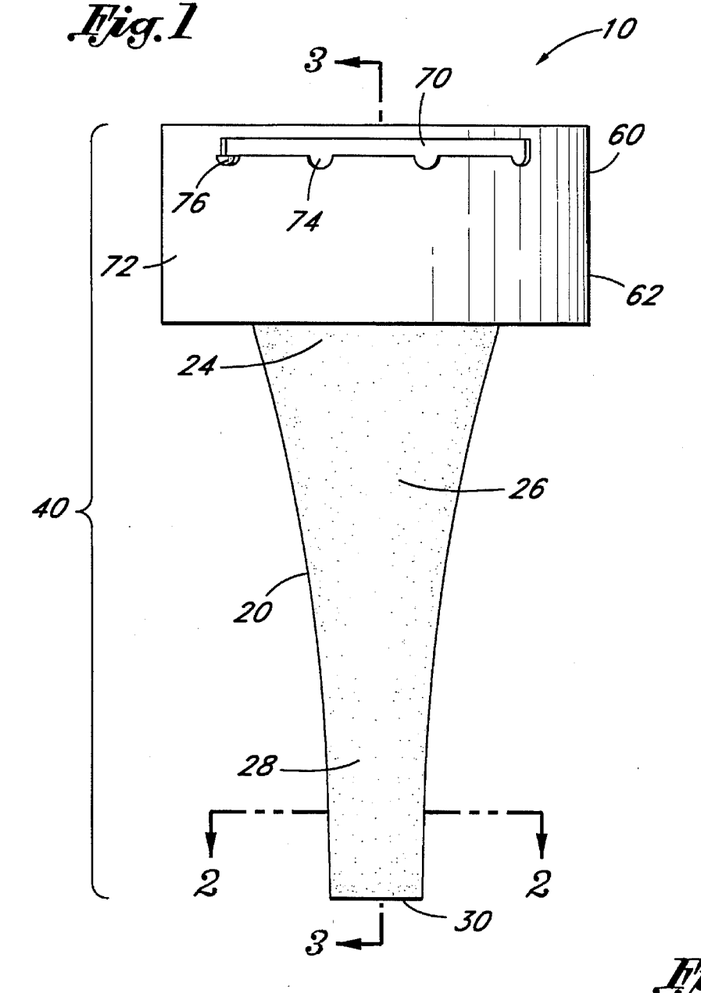
FIG. 1 is a side elevational view of one embodiment of the invention in the radially unexpanded state.
Figure 3:
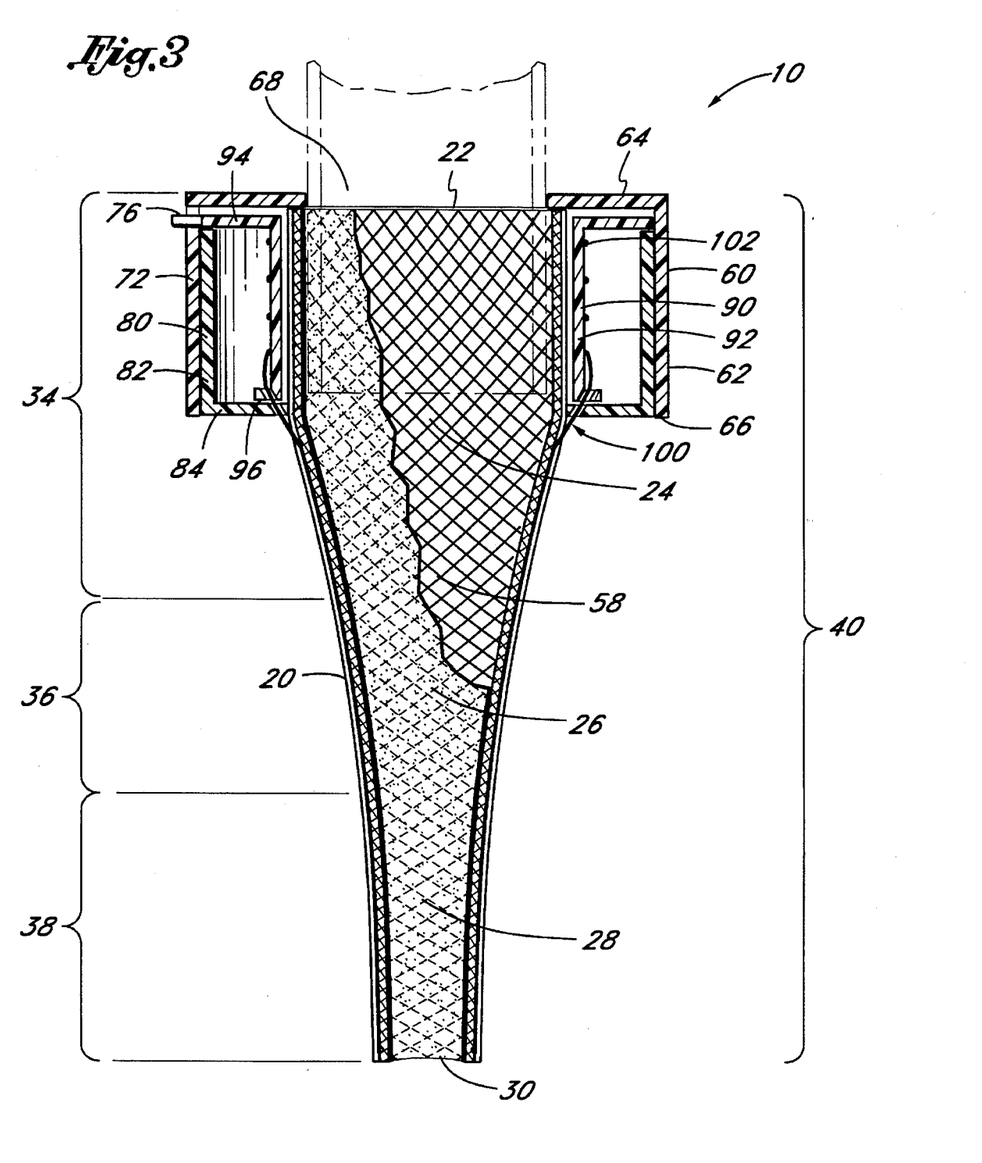
FIG. 3 is a cutaway, cross-sectional view taken along line 3—3 of FIG. 1.

Referring now to FIGS. 1 and 3, there is illustrated a surgical retractor according to one embodiment of the present invention in the radially unexpanded state. FIG. 1 shows an elevational view of the embodiment. FIG. 3 shows a cutaway, sagittal cross-sectional view of the embodiment taken along line 3—3 of FIG. 1.

As shown in FIGS. 1 and 3, the surgical retractor 10 has a radially expandable tubular body 20 and a control 60 for applying axial compressive force to the tubular body 20. The tubular body has a plurality of segments including at least a proximal segment 24 and a distal segment 28, and opposing ends comprising a proximal end 22 and a distal end 30.

The proximal segment 24 is located adjacent to the proximal end 22, and has an axial length 34. The distal segment 28 is located adjacent to the distal end 30, and has an axial length 38. In one particularly preferred embodiment, the distal end 30 is a blunt rather than a cutting surface, so that the distal end 30 will contact biological tissue atraumatically.

Additional segments of tubular body 20 can be present besides a proximal segment 24 and a distal segment 28. For example, as illustrated in FIG. 3, an additional segment such as a central segment 26 having an axial length 36, or other segments having axial lengths, can be located between the proximal segment and the distal segment. The sum of all axial lengths of each of the plurality of segments forming tube 20 constitute the axial length of the tubular body 40.

Figure 2:
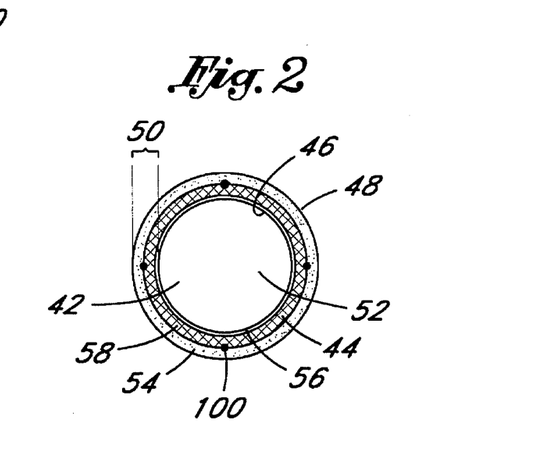
FIG. 2 is a cross-sectional view taken along line 2—2 of FIG. 1.

Referring now to FIG. 2, there is illustrated a transverse cross section of the tubular body 20 taken along line 2—2 in FIG. 1. As can be seen, tubular body 20 has an axial lumen 42 therethrough, and comprises a tubular wall 44. In this embodiment, tubular wall 44 completely surrounds the axial lumen 42. As used herein, "completely surrounds" means that tubular body 20 does not have an axially extending slit extending from proximal end 22 or distal end 30, towards the opposing end.

Tubular wall 44 has an internal surface 46 adjacent to the axial lumen 42 and an external surface 48 on the exterior of a tubular wall 44. A wall thickness 50 of the tubular body 20 constitutes a distance extending from the interior surface 46 to the exterior surface 48.

Axial lumen 42 is shown in FIG. 2 as substantially circular. However, as understood by those with skill in the art, the axial lumen 42 can also be elliptical, oval, or any other shape suitable for the intended purpose. Further, the shape of axial lumen 42 can vary over the length of tubular body 20. Axial lumen 42 has a cross-sectional area 52.

Tubular body 20 has a first cross-sectional area when no axial compressive force is applied and a second, larger cross-sectional area when compressive axial force is applied, up to a maximum cross-sectional area beyond which there is no increase in cross-sectional area upon the application of additional compressive force. Upon application of compressive axial force to the tubular body having a first cross-sectional area, there is a simultaneous shortening of the axial length 40 from a first axial length to a second shorter axial length, up to a minimum axial length beyond which there is no decrease in axial length upon the application of additional force.

In one preferred embodiment, tubular body 20 comprises mesh 58. The mesh can comprise any of a variety of elastic materials or nonelastic materials woven or braided into a structure such that when compressive axial force is applied to the mesh, it shortens in a direction parallel to the axial force and expands in a direction perpendicular to the axial force.

In a particularly preferred embodiment, tubular body 20 comprises mesh made of polymeric strands, such as polypropylene or nylon, or mesh made of a metal wire, such as stainless spring steel. The mesh can be formed by a weaving process, thermal molding or stamping as is appropriate for the particular material. Other suitable materials and configurations are known to those with skill in the art. Further, suitable mesh can be purchased commercially from a variety of sources, including Coleflex of West Babylon, N. Y.

In one preferred embodiment, tubular wall 44 comprises an external coating 54 surrounding the mesh 58, to provide a generally atraumatic tissue contacting surface. The external coating can be made of elastic, biocompatible material, such as latex or silicone, or of other suitable materials as are known to those with skill in the art. Application of the external coating 54 can be accomplished in any of a variety of ways known in the art. For example, spraying, dipping, or painting operations can be used, depending upon the viscosity of the coating precursor. Alternatively, the coating 54 can be provided in the form of a tubular sleeve, which is advanced axially over the mesh 58 while the mesh is in the first, reduced cross-sectional configuration.

In one particularly preferred embodiment, the external coating 54 is nonelectrically conducting. In addition, the external coating 54 can be impregnated with functional substances, such as a hemostatic agent, healing promoter or antibiotic.

Tubular wall 44 is optionally provided with an internal coating 56 for separating mesh 58 and axial lumen 42. The internal coating can be made of elastic, biocompatible material, such as latex or silicone, or of other suitable material as are known to those with skill in the art. In one particularly preferred embodiment, the internal coating is non-electrically conducting. In a particularly preferred embodiment, tubular wall 44 comprises both an external coating 54 and an internal coating 56.

Both external coating 54 and internal coating 56 can comprise multiple layers of the same or differing material, varying layer thicknesses, or varying types of material constituting a layer over the same or different tubular body segments. As used herein, the term "coating" should be construed to incorporate all of the foregoing possibilities and combinations thereof.

The external coating and internal coating advantageously serve to create a smooth, non-traumatic surface adjacent to the biological tissue. Further, they advantageously serve to isolate the contents of the axial lumen 42, such as instrumentation and substances being introduced and withdrawn from the axial lumen 42, from the biological tissue surrounding the surgical retractor 10.

Figure 4:
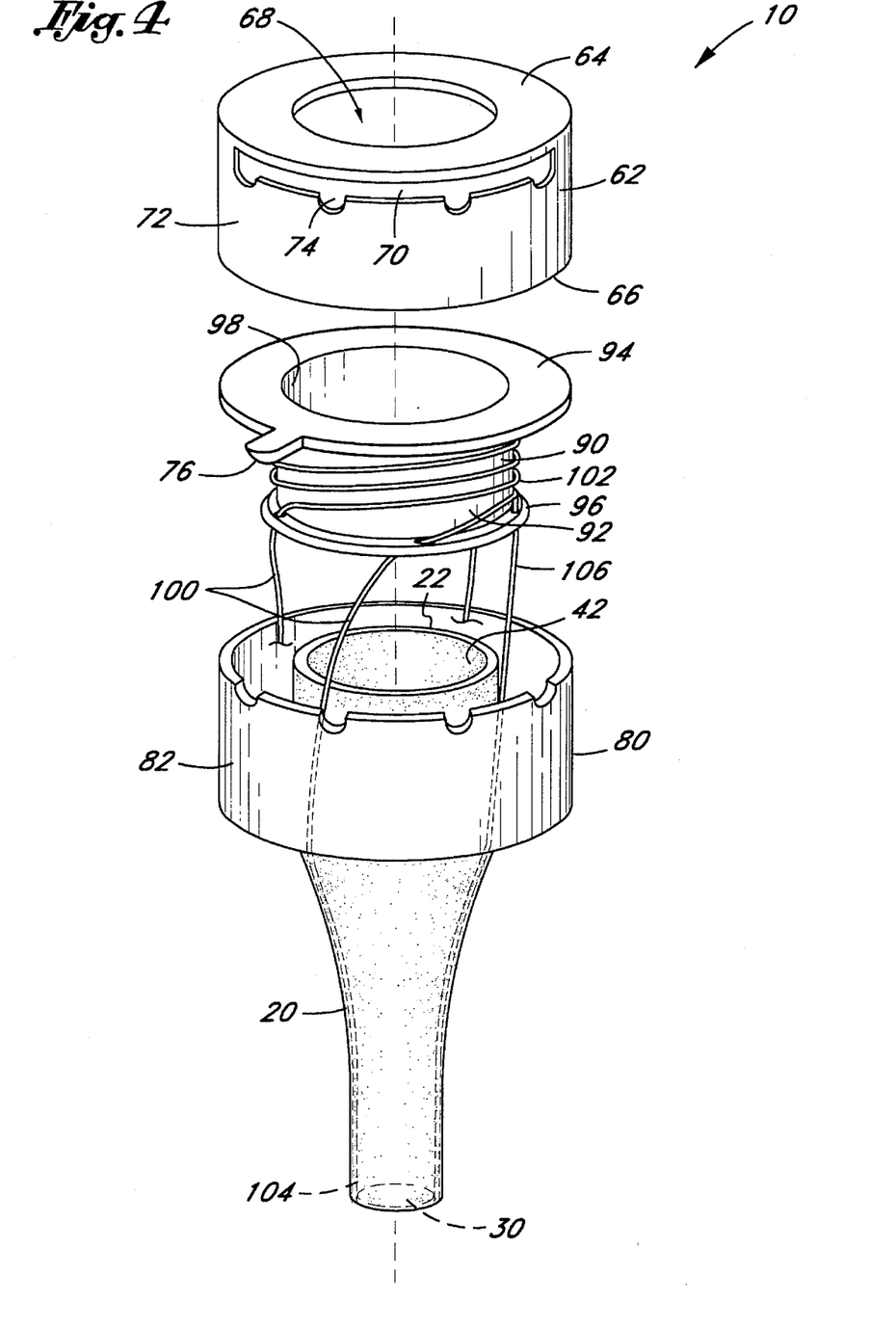
FIG. 4 is a perspective exploded view of one embodiment of the invention.

FIG. 4 is a perspective exploded view of the embodiment of the invention shown in FIGS. 1–3. Referring now to FIGS. 1, 3 and 4, a control 60 for applying axial compressive force to the tubular body 20 is connected to the proximal segment 24. The control depicted in FIGS. 1, 3 and 4 is by way of illustration only. Any of a variety of controls suitable for applying axial compressive force to tubular body 20 can be used, as will be understood by those with skill in the art in view of the disclosure herein.

In the embodiment illustrated in FIGS. 1, 3 and 4, the control 60 comprises a cap 62 having a substantially cylindrical lateral wall 72, a proximal endplate 64 and a distal end 66. Proximal endplate of the control 64 has a port 68 for accessing the axial lumen 42, therethrough.

In one preferred embodiment, the cross-sectional area of port 68 is at least as large as the largest cross-sectional area of the axial lumen 52 created upon the application of maximal axial compressive force. This configuration allows the placement of instrumentation into and the extraction of materials through axial lumen 42 having substantially the identical cross-sectional area as the largest cross-sectional area of the axial lumen 52.

Cap 62 of control 60 further comprises a slit 70 along its lateral wall 72. The relative length of the slit 70 compared to the other components of control 60 is by way of illustration only. As discussed below, the length is related to the total desired amount of shortening of axial length 40 of tubular body 20.

The slit 70 has at least one indentation or other stop 74. Preferably, slit 70 has a plurality of indentations. A detent 76 extends from the interior of the cap 62 exteriorly through slit 70. Preferably, detent 76 and indentation 74 are of such corresponding shapes that detent 76 will rest within indentation 74 until sufficient manual force is applied to detent 76 to disengage the detent 76 from the indentation 74.

In general, the cooperation of the detent 76 with indentations 74 provides a way of indexing the relative rotational position of the capstan 90, discussed below, and the cap 62. This rotational movement is translated into axial compressive force on the tubular body 20 through the use of a plurality of pull wires 100, discussed further below. As will be apparent to one of ordinary skill in the art, any of a wide variety of indexing structures can be readily adapted to provide audible or tactile feedback to the user relating to the relative rotational orientation of the control, and hence relative expansion of the tubular body 20.

Referring now to FIGS. 3 and 4, control 60 further comprises a housing 80 connected to the proximal segment 24 of tubular body 20. Housing 80 comprises a substantially cylindrical lateral wall 82 and a distal endplate 84. The substantially cylindrical lateral wall 82 has a cross-sectional area and shape such that it will fit within cap 62 as indicated in FIG. 3. The proximal segment 24 of tubular body 20 extends at least partially through housing 80, and can extend completely through housing 80 and cap 62 exiting port 68, as indicated by the phantom lines in FIG. 3.

Inside housing 80 is a capstan 90 having a substantially cylindrical wall 92 and a distal flange segment 96 connected to wall 92 at one axially end. As can be seen in FIG. 4, detent 76 is an extension of the proximal flange portion 94 of capstan 90. Optionally, a proximal flange segment 94 can be connected to wall 92 at an axially opposing end.

The substantially cylindrical wall 92 of capstan 90 has an axial lumen 98 having a cross-sectional area and cross-sectional shape such that the proximal segment 24 of tubular body 20 will fit within the substantially cylindrical wall 92.

The axial length of the cylindrical wall 92 of capstan 90 should be such that, when the capstan is seated upon the distal endplate 84 of housing 80, the detent 76 will extend above the proximal edge of housing 80, such that detent 76 can rotate laterally in slit 70 of cap 62 upon axial rotation of capstan 90.

The individual parts of control 60, that is cap 62, housing 80 and capstan 90, can be made of any suitable resilient material as will be understood by those with skill in the art in view of the disclosure herein. For example, suitable materials include steel and other metals, and thermoplastic resilient material that can be sterilized before use. Examples of such plastic include polyethylene, polypropylene, copolymers thereof, as well as polyvinyl chloride polymers or acrylic acid polymer and copolymers, that are inert to body fluids and medical liquids such as sterilants.

The control can be made by any of a variety of known thermoplastic manufacturing techniques, such as injection molding. Once produced, the individual components of the control and tubular body are assembled by techniques well known to those with skill in the art. For example, the control components and tubular body can be assembled using adhesives, fasteners, solvent bonding, or welding, as is be appropriate to the material.

The surgical retractor of the present invention can be either disposable, such as intended for a single use, or reusable a plurality of times or reusable indefinitely. However, in any case, it is necessary that materials that come in contact with a surgical incision be sterilizable. Components forming a reusable surgical retractor according to the present invention, must be repeatably sterilizable. Sterilization can be by gas, heat, radiation, chemical or other means, as is appropriate for the materials and as is understood by those with skill in the art.

Referring now to FIGS. 2–4, in one preferred embodiment, surgical retractor 10 additionally comprises a plurality of cables or pull wires 100 as a means for transferring energy from the control 60 to the tubular body 20, thereby increasing cross-sectional area 52 while shortening axial length 40 of tubular body 20. Though shown with four pull wires present, surgical retractor 10 can comprise any number of pull wires preferably greater than one pull wire. In one preferred embodiment, surgical retractor 10 comprises between three and six pull wires. In one particularly preferred embodiment, surgical retractor 10 comprises exactly four pull wires.

Each pull wire has a proximal end 102, a distal end 104 and a body 106. Each proximal end 102 is attached to the capstan 90 and each distal end 104 is attached to or linked through the distal segment 28 of tubular body 20. In one preferred embodiment, the distal ends 104 are attached to the mesh 58.

In a particularly preferred embodiment, each pull wire 100 extends distally from the capstan 90 and along the tubular body 20. At a relatively distal point along tubular body 20, the pull wire 100 is threaded through the mesh of the tubular body 20 to the other side thereof. The pull wire 100 thereafter loops back in the proximal direction, where it is secured to the capstan 90 or other suitable point of attachment on the control 60. In this manner, the risk of a separation at a distal joint between the pull wire 100 and the tubular body 20 is minimized. The two segments of the pull wire 100 that extend proximally along the tubular body 20 from the point at which pull wire 100 is threaded through the tubular body 20 can extend either on the radial outside surface of the mesh 58, the radial inside surface of the mesh 58, or one segment on each side of the mesh 58, as will be apparent to one of skill in the art. The use of an internal coating 56 is particularly desirable if one or more of the segments of the looped pull wire 100 extends axially along the radial interior surface of the mesh 58. This minimizes the risk that medical instruments extending through axial lumen 42 become entangled in the pull wire 100.

Pull wires 100 can comprise any of a number of relatively axially nonstretchable materials well known to those with skill in the art that are capable of transmitting sufficient pulling force along their axes. In one preferred embodiment, pull wires 100 comprise steel or titanium wire, nylon, or other synthetic thread. Both wire and thread can be either single stranded or multiple strands woven to impart sufficient strength or for other reasons such as to improve lateral flexibility, as is understood by those skilled in the art.

Means of attachment of pull wires 100 to both tubular body 20 and capstan 90 will depend on the materials used for tubular body 20 and capstan 90, as well as pull wires 100. A variety of means are available as is understood by those with skill in the art. For example, pull wires 100 can be soldered to tubular body 20 or capstan 90 if all components are made from a suitable metal. Alternately, pull wires 100 can be fixed to an attachment point on capstan 90 by hooks, knots, or the like (not illustrated), or to the tubular body mesh 58 by hooks engaging the mesh 58.

Operation of surgical retractor 10 is accomplished by first inserting the distal end 30 of tubular body 20 into a surgical incision, such as an incision into the integument, or into a body opening such as the anus or nasal antrum, when the tubular body is in a state of relaxed axial compressive force such that at least one segment of the tubular body in placed within the incision or opening while the control 60 remains external to the incision. The incision can also be made in an organ or other biological tissue.

In one preferred embodiment, the distal end 30 of surgical retractor 10 is adapted for atraumatic contact with a biological tissue. This adaptation can be accomplished by assuring that the distal end 30 of the tubular body 20 and exterior surface of the tubular body 48 are substantially smooth and comprise biocompatible material, such as silicone. This feature of the present invention allows the surgical retractor to be used in situations where a cutting surface on the distal end of a retractor would injure underlying structures to the detriment of the patient.

For example, in situations where the incision is made directly above a site of a suspected cancer or over a major blood vessel, having an atraumatic distal end minimizes the risk of rupture of a tumor mass with release of cells into the surrounding tissue or the unintentional puncture of the blood vessel. Related to this latter advantage, the present invention can be used with particular effectiveness when combined with the device for sealing blood vessels disclosed in co-pending U.S. application Ser. No. 08/127,769, the disclosure of which is hereby incorporated in its entirety by reference.

After insertion of at least one segment of the tubular body 20 into the incision or other opening, the next step in operating the surgical retractor is to actuate control 60 by manually rotating detent 76 counterclockwise within slit 70 from an initial indentation 74 until detent 76 engages at least one indentation 74 rotationally displaced from the initial indentation. Hence, the actuation advantageously does not require a source of gas or liquid, as is required by other retractors.

Movement of the indent 76 through slit 70 rotates capstan 90 counterclockwise through at least one of a plurality of discrete rotational angles causing pull wires 100 to wind around capstan 90, thus placing axial compressive force, or additional axial compressive force, on tubular body 20. As will be appreciated by those with skill in the art, each pull wire is rotatably fixed to the housing 80 or proximal segment of the tubular body 24 to allow transmission of the force applied to capstan 90 to be transferred to tubular body 20. The axial compressive force or additional axial compressive force on tubular body 20 causes the axial length 40 of tubular body 20 to shorten from a first axial length to a second shorter axial length while simultaneously increasing the cross-sectional area 52 of tubular body 20 from a first smaller cross-sectional area to at least one of a plurality of second larger cross-sectional areas. The increase in cross-sectional area 52 of tubular body 20 moves the edges of the incision apart allowing visualization of and access to the underlying tissues for diagnostic and therapeutic procedures.

As will be appreciated by those with skill in the art, the greater the circumferential length of slit 70, the greater the rotational travel of indent 76. Therefore, the length of slit 70 determines the total possible amount of rotation of capstan 90. The amount of rotation of a capstan 90 of a particular diameter further determines the amount of uptake of pull wires 100 around capstan 90, thereby determining the decrease in axial length 40 of tubular body 20 and the simultaneous increase in the cross-sectional area of at least one segment of tubular body 20. Hence, the longer the slit 70, the greater the possible decrease in axial length 40 and the greater the possible simultaneous increase in cross-sectional area of at least one segment of tubular body 20.

In one preferred embodiment, the length of slit 70 is between about 10 percent and 80 percent of the circumference of cap 62. In another preferred embodiment, the length of slit 70 is between about 25 percent and 60 percent of the circumference of cap 62. In one particularly preferred embodiment, the length of slit 70 is about 50 percent of the circumference of cap 62.

Further, slit 70 can comprise a spiral orientation, not illustrated, relative to the lateral wall 72 of cap 62, particularly to allow axial travel of indent 76 more than one complete circumference around cap 62. This embodiment would be particularly useful in an embodiment having a relatively small diameter capstan 90, or when it is otherwise necessary to achieve the desired degree of shortening of axial length 40. The necessary modifications of control 60 to allow travel of indent 76 in a spirally oriented slit 70 are understood by those of skill in the art.

Any of a variety of alternate structures can also be used, to accomplish a reversible axial proximal displacement of the pull wires 100. For example, the proximal ends of the pull wires 100 can be connected to a threaded member such as a nut, threadably engaged on an axially extending rotatable threaded shaft. Rotation of the shaft will cause axial displacement of the pull wires 100. Alternatively, any of a variety of threaded and/or ramped structures can be utilized, which convert rotational or compressive forces to axial displacement, as will be readily appreciated by one of skill in the art.

Once the edges of the incision are separated allowing visualization of and access to the underlying tissues, diagnosis or treatment is then performed. Once diagnosis or treatment is completed, control 60 is actuated by manually rotating detent 76 clockwise within slit 70 until detent 76 is returned to its original rotational orientation. This movement of the indent 76 rotates capstan 90 clockwise through at least one of a plurality of discrete rotational angles causing pull wires 100 to unwind around capstan 90, thus reducing or eliminating axial compressive force, or additional axial compressive force, on tubular body 20. The reduced axial compressive force on tubular body 20 causes the axial length 40 of tubular body 20 to lengthen from a first axial length to a second longer axial length while simultaneously decreasing the cross-sectional area 52 of tubular body 20 from a first larger cross-sectional area to at least one of a plurality of second smaller cross-sectional area. Finally, the surgical retractor is then removed from the incision.

The application of axial compressive force to tubular body 20 is indicated in the Figures as occurring though counterclockwise rotation of capstan 90 and the reduction of axial compressive force to tubular body 20 is indicated in the Figures as occurring though clockwise rotation of capstan 90. However, as would be understood by those with skill in the art, clockwise motion of a capstan configured in a reverse orientation can also be used to apply axial compressive force to tubular body 20 and counterclockwise motion of a capstan configured in a reverse orientation can also be used to reduce the axial compressive force on tubular body 20.

Figures 5, 6:
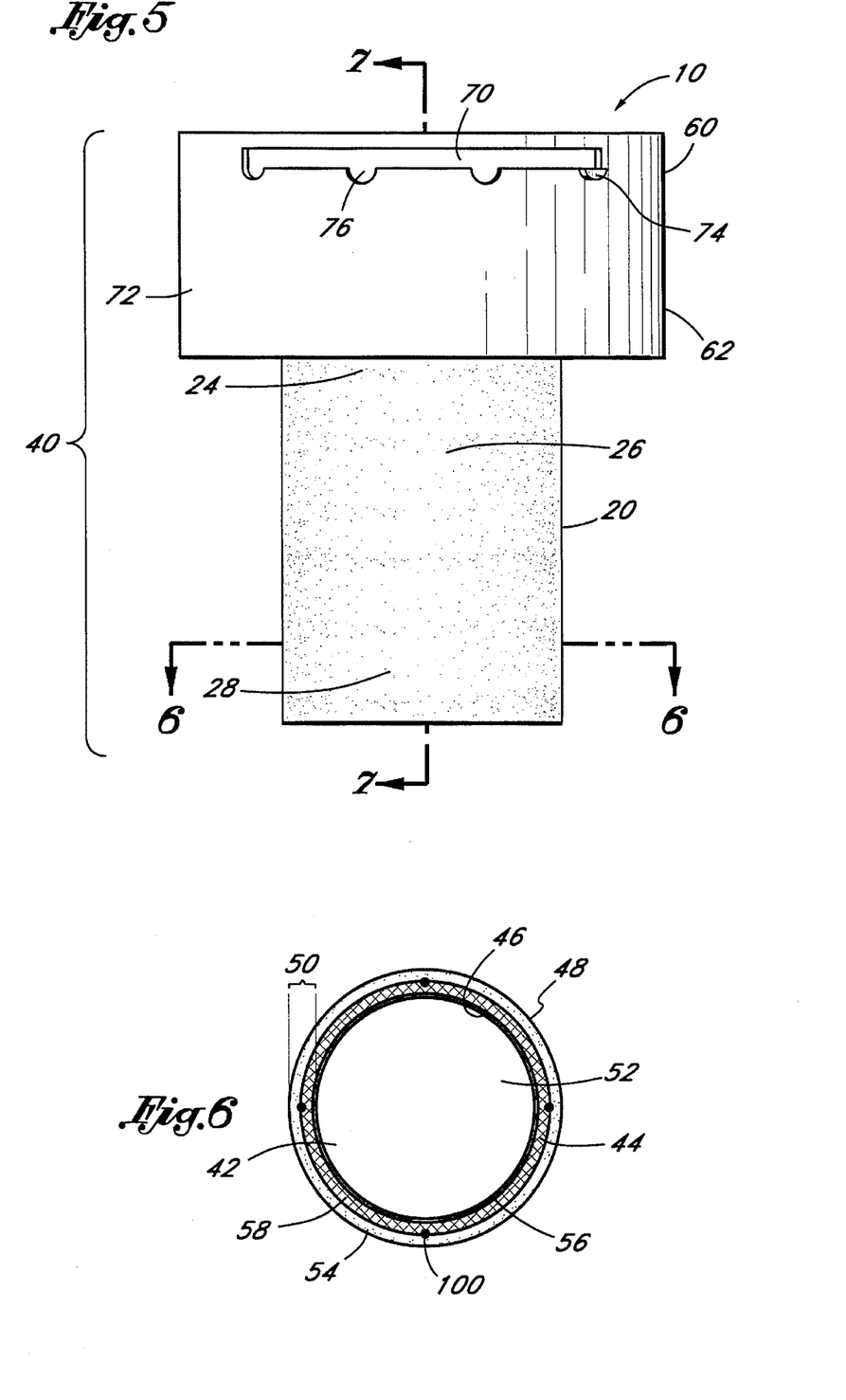
FIG. 5 is a side elevational view of one embodiment of the invention in a radially expanded state.
FIG. 6 is a cross-sectional view taken along line 6—6 of FIG. 5.
Figure 7:
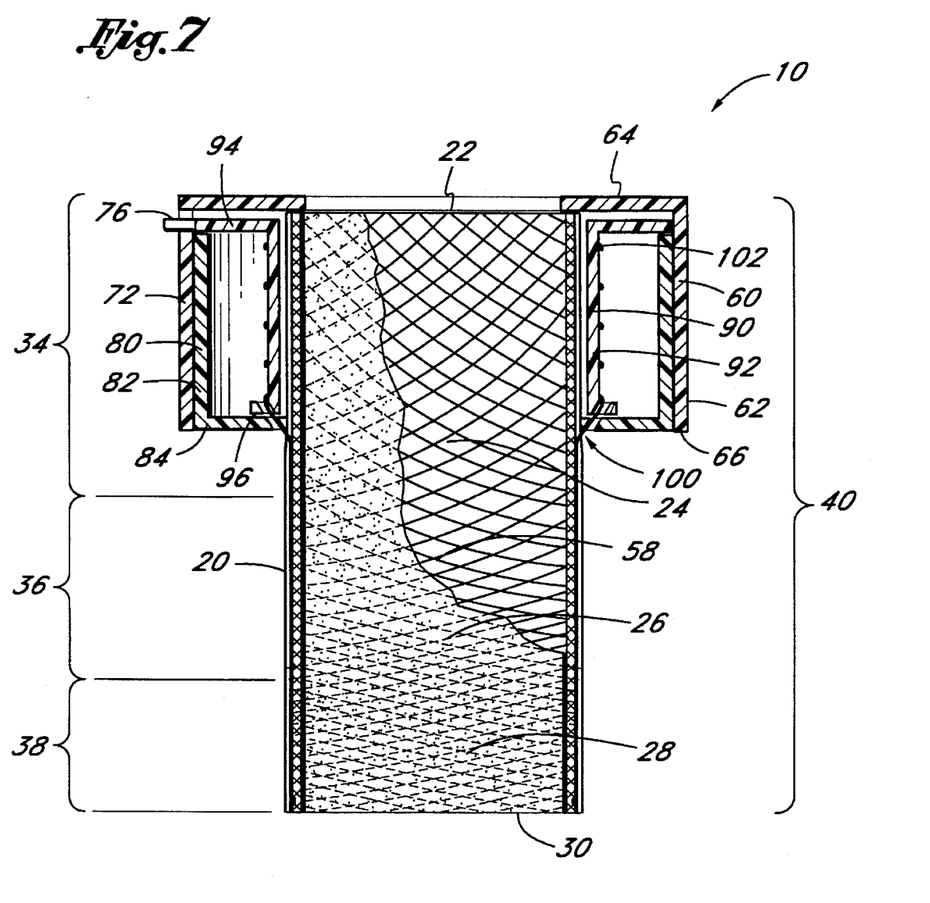
FIG. 7 is a cutaway, cross-sectional view taken along line 7—7 of FIG. 5.

Referring now to FIGS. 5–7, there is illustrated a surgical retractor according to the present invention which has had maximal application of axial compressive force to tubular body 20 by winding pull wires 100 around capstan 90. FIG. 5 is an elevational view of the embodiment of the invention shown in FIGS. 1–3. FIG. 6 illustrates a transverse cross-sectional view taken along line 6—6 of FIG. 5. FIG. 7 illustrates a cutaway, sagittal cross-sectional view taken along line 7—7 of FIG. 5.

As can be seen in FIGS. 5 and 7, application of axial compressive force to tubular body 20 causes the axial length 40 of tubular body 20 to shorten compared to the axial length 40 of tubular body 20 shown in FIGS. 1 and 3.

As can be seen in FIG. 6, application of axial compressive force to tubular body 20 causes a simultaneous increase in the cross-sectional area of the cross-sectional area 52 of tubular lumen 42 as compared with the cross-sectional area 52 of tubular lumen 42 illustrated in FIG. 2. In this embodiment, the tubular body 20 in the expanded state exhibits a substantially cylindrical profile. Incision expanders, in accordance with the present invention, can be readily configured, such that the radially enlarged configuration produces a profile other than cylindrical, such as will be discussed in connection with FIGS. 8 and 9 below.

As can be seen in FIGS. 3 and 7, axial compression of the tubular body 20 from a first length to a second length causes dissimilar radial expansion between the proximal segment cross-sectional area, the central segment cross-sectional area, and the distal segment cross-sectional area.

In one preferred embodiment, illustrated in FIG. 2 and FIG. 6, the wall thickness 50 remains substantially unchanged upon the application of axial compressive force. This feature is advantageous in that it contributes to a maximal cross-sectional area 52 of tubular lumen 20 upon application of axial compressive force to allow for maximal visualization of and access to underlying tissues and structures.

In one particularly preferred embodiment, the wall thickness 50 is kept at a minimal percent of the cross-sectional area 42 by choosing materials comprising the components of tubular wall 44 with the minimal thicknesses while still retaining adequate strength and other properties necessary to perform the function of the present invention.

Suitable dimensions and proportions of the surgical retractor, according to one aspect of the present invention, are given for exemplary purposes only as follows. The axial length of the tubular body, in the radially unexpanded state, is between about 1 cm and 10 cm long. In a preferred embodiment, the axial length of the tubular body, in the radially unexpanded state, is between about 3 cm and 7 cm long. In a particularly preferred embodiment, the axial length of the tubular body, in the radially unexpanded state, is about 5 cm.

The axial length of the tubular body, in the radially maximally expanded state, is between about 0.5 cm and 7 cm long. In a preferred embodiment, the axial length of the tubular body, in the radially maximally expanded state, is between about 2 cm and 5 cm long. In a particularly preferred embodiment, the axial length of the tubular body, in the radially maximally expanded state, is about 3 cm.

The cross-sectional area of the distal segment of the tubular body, in the radially unexpanded state, is between about 0.25 $cm^2$ and 5 $cm^2$. In a preferred embodiment, the cross-sectional area of the distal segment of the tubular body, in the radially unexpanded state, is between about 0.5 $cm^2$ and 3 $cm^2$. In a particularly preferred embodiment, the cross-sectional area of the distal segment of the tubular body, in the radially unexpanded state, is about 1 $cm^2$.

The cross-sectional area of the distal segment of the tubular body, in the radially maximally expanded state, is between about 0.5 cm$^2$ and 10 cm$^2$. In a preferred embodiment, the cross-sectional area of the distal segment of the tubular body, in the radially unexpanded state, is between about 1 cm$^2$ and 6 cm$^2$. In a particularly preferred embodiment, the cross-sectional area of the distal segment of the tubular body, in the radially unexpanded state, is about 3 cm$^2$.

The wall thickness of the tubular body is between about 0.1 cm and 0.5 cm. In a preferred embodiment, the wall thickness of the tubular body is between about 0.2 cm and 0.4 cm. In a particularly preferred embodiment, the wall thickness of the tubular body is about 0.3 cm.

The dimensions of the control are suitable to allow manual actuation of the control of the surgical retractor. For example, the control is between about 1 cm and 5 cm in axial height and between about 3 cm$^2$ and 10 cm$^2$ in cross-sectional area. In a preferred embodiment, the control is between about 2 cm and 4 cm in axial height and between about 5 cm$^2$ and 7 cm$^2$ in cross-sectional area. In a particularly preferred embodiment, the control is about 3 cm in axial height and about 6 cm$^2$ in cross-sectional area. Surgical retractors having larger or smaller dimensions, or other relative proportions are included within the scope of this invention.

Figure 8:
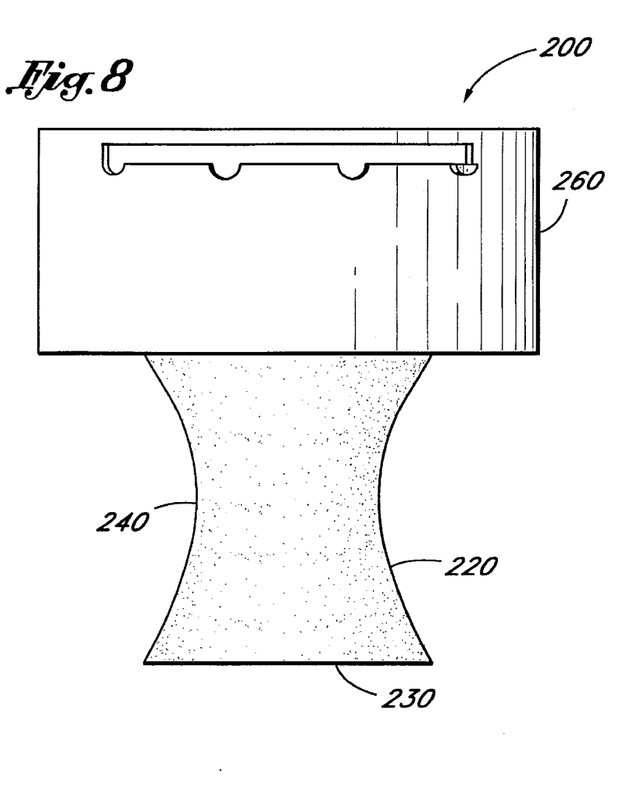
FIG. 8 is an elevational view of an alternate embodiment of the invention in the radially expanded state.
Figure 9:
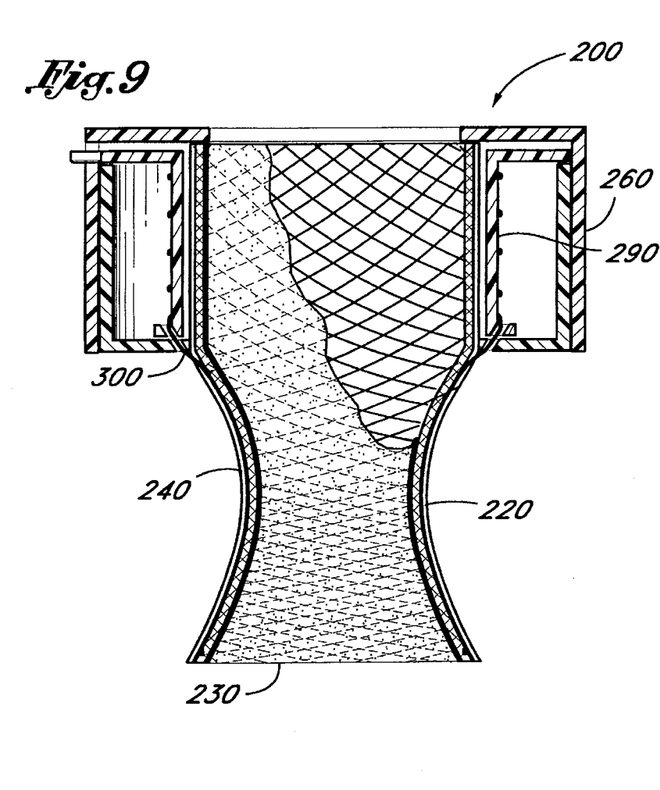
FIG. 9 is a cutaway, cross-sectional view taken along line 9—9 of FIG. 8.

Referring now to FIGS. 8 and 9, there is illustrated a surgical retractor 200, according to a further embodiment of the present invention, comprising a tubular body 220 and control 260. FIG. 8 is a perspective view of the embodiment and FIG. 9 is a cutaway, cross-sectional view taken along line 9—9 of FIG. 8. As illustrated, axial compressive force has been applied to tubular body 220 through the winding of pull wires 300 around capstan 290 to place tubular body 220 in the radially expanded state.

Note that tubular body 220 has radially expanded to a larger cross-sectional area at its distal end 230, than at its middle 240. This uneven radially expansion can be accomplished by using different materials, thicknesses or number of layers to produce varying segments of tubular body 220 as is understood by those with skill in the art. Greater radial expansion at the distal end 230 of tubular body 220, compared to the middle 240 of tubular body 220, can be an advantage, such as during use with the device for sealing blood vessels disclosed in co-pending U.S. patent application Ser. No. 08/127,769.

In summary, the device for percutaneously delivering a tissue adhesive to the surface of a perforated vascular wall disclosed in co-pending U.S. patent application Ser. No. 08/127,769 comprises a tubular housing having a proximal control end and a distal delivery end. The tubular housing has a reservoir for containing a volume of tissue adhesive and an applicator on the distal delivery end in fluid communication with the reservoir for applying tissue adhesive to the surface of a perforated vascular wall. The device further comprises a control for expressing adhesive from the reservoir to the applicator.

The device for percutaneously delivering a tissue adhesive to the surface of a perforated vascular wall can further comprise a piston in the reservoir for expressing tissue adhesive from the reservoir to the applicator and a stop for limiting the travel of the piston, in order to set a predetermined maximum delivered volume of tissue adhesive. Additionally, the device can further comprise a valve disposed in the flow path between the reservoir and the delivery surface, for sealingly retaining the tissue adhesive within the reservoir.

Suitable tissue adhesives for use with the device for percutaneously delivering a tissue adhesive include methyl cyanoacrylate, ethyl cyanoacrylate, n-propyl cyanoacrylate, isopropyl cyanoacrylate, n-butyl cyanoacrylate, isobutyl cyanoacrylate, n-amyl cyanoacrylate, isoamyl cyanoacrylate, 3-acetoxypropylcyanoacrylate, 2-methoxypropylcyanoacrylate, 3-chloropropyl cyanoacrylate, benzyl cyanoacrylate, phenyl cyanoacrylate, alkenyl cyanoacrylate, butyl-2-cyanoacrylate, alkoxyalky 2-cyanoacrylates, fluorinated 2-cyanoacrylates or combinations thereof.

The device for percutaneously delivering a tissue adhesive to the surface of a perforated vascular wall can be used to inhibit vascular hemorrhage, such as from a coronary angioplasty catheter access site in a femoral artery, by placing the device through the integument opening at the access site over the perforated vascular wall, discharging tissue adhesive from the reservoir and removing the device. The applicator is designed to deliver the adhesive around the opening of the vascular puncture, rather than through it, by providing a blunt, ball tip to contact the site.

Returning now to our discussion of the present invention, embodiments of the surgical retractor disclosed above, tubular body 20 completely surrounds the axial lumen 42. This configuration has several advantages. One advantage is that instrumentation can be passed through the axial lumen 80 without contacting the sides of the incision. Therefore, advantageously, the instrumentation will not tend to shred the biological tissue lining the sides of the incision or opening, such as fat or mucosa, thereby not increasing the chances of post-operative wound infection.

Further, the withdrawal of any biological tissues through the axial lumen 42 will similarly not contact the sides of the incision or opening. This will tend to prevent the spread of cancer or infections through a surgical tract, as is a potential problem during the removal of tumors in laparoscopy through laparoscopic incisions, and in the drainage of infected tissues.

In one preferred embodiment, a stopper, not illustrated, can be supplied to fit in port 68 or axial lumen 42 at the proximal end 22. This stopper would be useful to prevent the undesirable introduction of, or escape of, materials through axial lumen 42 from the cavity accessed by the retractor according to one embodiment of the present invention. For example, the stopper can be in place to prevent the escape of gas from the abdomen during laparoscopy as the retractor is inserted and the stopper removed to allow the insertion of instrumentation into the abdomen through axial lumen 42.

In one preferred embodiment, a flange, not illustrated, can extend from the distal end 66 of cap 62 or distal endplate 84 of housing 80. The flange can be a circumferentially continuous or circumferentially discontinuous. It is anticipated that the flange will extend substantially perpendicular to the axial lumen. The flange alternately can be attached to the proximal segment of the tubular body 24.

The flange can have any of several purposes as will be understood by those with skill in the art. For example, it can allow a greater surface area of contact with the skin surrounding the incision. This would be useful in cases where the biological tissue surrounding the incision or opening is diseased or friable and would prevent trauma to the tissue. Further, the flange would assist in preventing external pressure on the surgical retractor from pushing the surgical retractor through an incision into an underlying body cavity. For example in cases where the surgical retractor is being used to expand a laparoscopy incision, the flange would reduce any tendency to push the surgical retractor through the laparoscopy incision and into the abdominal cavity.

In one preferred embodiment, the surgical retractor of the present invention additionally comprises a tubular sheath, surrounding tubular body 20. The tubular sheath can have the same internal structure as any of the embodiments of tubular body 20 and is connected to tubular body 20 at either the proximal segment 24 or distal segment 26 by adhesives, connectors or solder, or by other means appropriate to the materials as is understood by those with skill in the art. The tubular sheath can be used to isolate pull wires 100 from the sides of the surgical incision or opening, such as in place of the external coating 54.

Although this invention has been described in terms of certain preferred embodiments, other embodiments that are apparent to those of ordinary skill in the art are also within the scope of this invention. Accordingly, the scope of the invention is intended to be defined only by reference to the appended claims.

What is claimed is:

1. A surgical retractor capable of reversibly expanding an incision in biological tissue from a first cross-sectional area to a second larger cross-sectional area, comprising:
    a radially expandable tubular body having a radially expandable axial lumen therethrough, a tubular wall surrounding the axial lumen, the tubular wall having an interior surface adjacent the axial lumen and an exterior surface on the radial exterior of the tubular wall, a wall thickness between the interior surface and the exterior surface, opposing axial ends, one of which is a proximal end and the other of which is a distal end, wherein the distal end is provided with an atraumatic tip, a first axial length between the proximal end and the distal end, and at least two segments, wherein at least one segment is a proximal segment adjacent to the proximal end and at least an additional segment is a distal segment adjacent to the distal end; and
    a control for applying an axially compressive force to the tubular body thereby reversibly expanding the axial lumen by reversibly expanding at least one segment of the tubular body from a first cross-sectional area to at least one second larger cross-sectional area while simultaneously shortening the axial length of the tubular body from the first axial length to at least one second shorter axial length, the control being connected to the proximal segment.

2. A surgical retractor according to claim 1, wherein the exterior surface of the tubular body is biocompatible and substantially smooth.

3. A surgical retractor according to claim 1, wherein axial compression of the tubular body from the first length to the second length causes dissimilar radial expansion between the proximal segment cross-sectional area and the distal segment cross-sectional area.

4. A surgical retractor according to claim 1, further comprising a central segment between the proximal segment and distal segment, wherein axial compression of the tubular body from the first length to the second length causes dissimilar radial expansion between the proximal segment cross-sectional area and the central segment cross-sectional area.

5. A surgical retractor according to claim 1, further comprising a central segment between the proximal segment and distal segment, wherein the central segment has a cross-sectional area, and wherein axial compression of the tubular body from the first length to the second length causes dissimilar radial expansion between the central segment area and the distal segment.

6. A surgical retractor according to claim 1, wherein the tubular body comprises a woven mesh.

7. A surgical retractor according to claim 6, wherein the mesh comprises at least one material selected from the group consisting of steel, nylon and polypropylene.

8. A surgical retractor according to claim 6, further comprising at least one pull wire, said pull wire having a proximal end and a distal end, wherein the proximal end is connected to the control and wherein the distal end is connected to the distal segment of the tubular body.

9. A surgical retractor according to claim 8, comprising four pull wires.

10. A surgical retractor according to claim 8, wherein said at least one pull wire extends distally from the control along the mesh, through the mesh, and then proximally along the mesh back toward the control.

11. A surgical retractor according to claim 1, wherein the tubular body comprises at least one coating covering the interior surface of the tubular body.

12. A surgical retractor according to claim 11, wherein the at least one coating is selected from the group consisting of latex and silicone.

13. A surgical retractor according to claim 1, wherein the tubular body comprises at least one coating covering the exterior surface of the tubular body.

14. A surgical retractor according to claim 13, wherein the at least one coating is selected from the group consisting of latex and silicone.

15. A surgical retractor according to claim 1, wherein the tubular body wall thickness remains substantially unchanged when the tubular body is expanded from the first cross-sectional area to the second larger cross-sectional area.

16. A surgical retractor according to claim 1, further comprising a tubular sheath disposed adjacent the exterior surface of the tubular body.

17. A method of expanding an incision or puncture in biological tissue from a first cross-sectional area to a second larger cross-sectional area, comprising the steps of:
    (a) providing a surgical retractor according to claim 1;
    (b) placing at least one segment of the surgical retractor into an incision in biological tissue; and
    (c) actuating the control causing expansion of at least a portion of the axial lumen due to expansion of the tubular body from a first cross-sectional area to a second larger cross-sectional area while simultaneously shortening the axial length of the tubular body, thereby causing a corresponding expansion in the incision.

18. A method of treating a mammal, comprising the steps of:
    (a) providing a surgical retractor according to claim 1;
    (b) placing at least one segment of the surgical retractor into an opening in biological tissue of the mammal;
    (c) actuating the control to cause radial expansion of at least one portion of the axial lumen due to radial expansion of the tubular body from a first cross-sectional area to a second larger cross-sectional area while simultaneously shortening the axial length of the tubular body, thereby causing a corresponding expansion in the opening;
    (d) inserting an instrument into the axial lumen to effectuate treatment;
    (e) removing the instrument;
    (f) actuating the control to cause radial contraction of said at least one portion of the axial lumen due to radial contraction of the tubular body from the second larger cross-sectional area to a smaller cross-sectional area while simultaneously lengthening the axial length of the tubular body, thereby permitting a corresponding contraction in the opening; and (g) removing the surgical retractor from the opening.

19. An adjustable puncture expander, comprising:

a radially expandable tubular body having a radially expandable axial lumen therethrough, the tubular body having a proximal end and a distal end, the distal end having an axially facing radially expandable aperture in communication with said axial lumen, the axial lumen being expandable from a first cross-sectional area to a second, larger cross-sectional area upon axial compression of said tubular body;

a control on the proximal end of the tubular body; and at least two pull wires extending distally from the control to a point of attachment to the tubular body;

wherein activation of the control to advance the pull wires in an axial, proximal direction causes an axial compression of the tubular body and radial expansion of at least a distal segment of the axial lumen from the first cross-sectional area to the second cross-sectional area, thereby causing a corresponding expansion of at least the axially facing aperture at the distal end of the tubular body.

20. An adjustable puncture expander as in claim 19, wherein the tubular body comprises an expandable tubular mesh.

21. An adjustable puncture expander as in claim 20, wherein at least one of the pull wires extends distally along the mesh from the control, through the mesh, and then proximally along the mesh back toward the control.

22. An adjustable puncture expander as in claim 20, further comprising a tubular elastic sleeve surrounding the tubular mesh.

23. A surgical retractor capable of reversibly expanding an incision in biological tissue from a first cross-sectional area to a second larger cross-sectional area, comprising:

a radially expandable tubular body comprising a woven mesh, the tubular body having an axial lumen therethrough, a tubular wall surrounding the axial lumen, the tubular wall having an interior surface adjacent the axial lumen and an exterior surface on the radial exterior of the tubular wall, a wall thickness between the interior surface and the exterior surface, opposing axial ends, one of which is a proximal and the other of which is a distal end, wherein the distal end is provided with an atraumatic tip, a first axial length between the proximal end and the distal end, and at least two segments, wherein at least one segment is a proximal segment adjacent to the proximal end and at least an additional segment is a distal segment adjacent to the distal end;

a control for applying an axially compressive force to the tubular body thereby reversibly expanding at least one segment of the tubular body from a first cross-sectional area to at least one second larger cross-sectional area while simultaneously shortening the axial length of the tubular body from the first axial length to at least one second shorter axial length, the control being connected to the proximal segment; and at least one pull wire, said pull wire having a proximal end and a distal end, wherein the proximal end is connected to the control and wherein the distal end is connected to the distal segment of the tubular body.

24. A surgical retractor according to claim 23, comprising four pull wires.

25. A surgical retractor according to claim 23, wherein said at least one pull wire extends distally from the control along the mesh, through the mesh, and then proximally along the mesh back toward the control.

26. An adjustable puncture expander, comprising:

a radially expandable tubular body comprising an expandable tubular mesh, the tubular body having a proximal end and a distal end and being expandable from a first cross-sectional area to a second, larger cross-sectional area upon axial compression thereof;

a tubular elastic sleeve surrounding the tubular mesh;

a control on the proximal end of the tubular body; and at least two pull wires extending distally from the control to a point of attachment to the tubular body;

wherein activation of the control to advance the pull wires in an axial, proximal direction causes an axial compression of the tubular body and radial expansion of at least a segment of the tubular body from the first cross-sectional area to the second cross-sectional area.

* * * * *